United States Patent

Brossi et al.

[11] 3,933,827
[45] Jan. 20, 1976

[54] 9-ACYLOXY-5,11-DIMETHYL-6H-PYRIDO[4,3-B]CARBAZOLES

[75] Inventors: Arnold Brossi, Riehen, Switzerland; Robert William Guthrie, Fairfield; Richard Wightman Kierstead, North Caldwell, both of N.J.

[73] Assignee: Hoffmann-La Roche Inc., Nutley, N.J.

[22] Filed: Oct. 29, 1974

[21] Appl. No.: 518,308

[52] U.S. Cl................ 260/287 C; 424/258
[51] Int. Cl.².................... C07D 471/04
[58] Field of Search............ 260/287 R, 287 O

[56] References Cited
UNITED STATES PATENTS
3,772,306   11/1973   Morrison et al. ............ 260/287 R OTHER PUBLICATIONS
Dalton et al., "Aust. J. Chem." 20(12) 2715–2727, 1967.
Svoboda et al., "J. Pharm. Sci." 1968, 57(10), 1720–1725.

Primary Examiner—Richard J. Gallagher
Assistant Examiner—David E. Wheeler
Attorney, Agent, or Firm—Samuel L. Welt; Bernard S. Leon; William G. Isgro

[57] ABSTRACT

9-Acyloxy-5,11-dimethyl-6H-pyrido[4,3-b]carbazoles of the formula

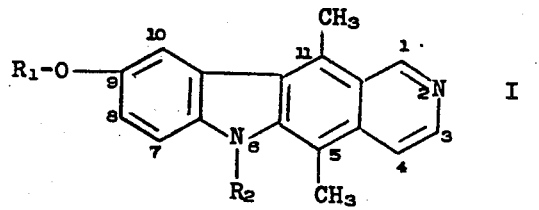

wherein $R_1$ is acyl and $R_2$ is hydrogen or lower alkyl, are described. The end products actively inhibit the growth of transplantable tumors, and are therefore useful as cytostatic agents.

13 Claims, No Drawings

9-ACYLOXY-5,11-DIMETHYL-6H-PYRIDO[4,3-B]CARBAZOLES

BRIEF SUMMARY OF THE INVENTION

The invention relates to 9-acyloxy-5,11-dimethyl-6H-pyrido[4,3-b]-carbazoles of the formula

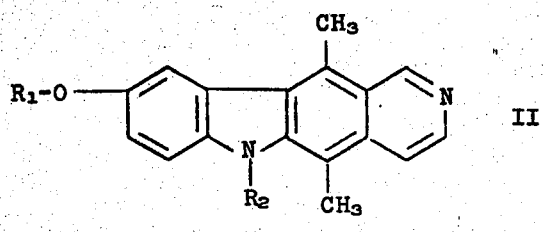

wherein $R_1$ is acyl and $R_2$ is hydrogen or lower alkyl, and pharmaceutically acceptable acid addition salts thereof. The end products are useful as cytostatic agents.

DETAILED DESCRIPTION OF THE INVENTION

The invention comprises novel 9-acyloxy-5,11-dimethyl-6H-pyrido-[4,3-b]carbazoles. As used herein, the term "lower alkyl" denotes a straight or branched chain saturated hydrocarbon containing 1–7 carbon atoms, for example, methyl, ethyl, propyl, isopropyl, butyl, t-butyl, neopentyl, pentyl, heptyl, and the like. The term "lower alkoxy" denotes an alkyl ether group in which the lower alkyl group is as described above, for example, methoxy, ethoxy, propoxy, pentoxy, and the like. The term "acyl" denotes an alkanoyl group derived from an aliphatic carboxylic acid of 1–18 carbon atoms, preferably from 1–7 carbon atoms, for example, formyl, acetyl, hexanoyl, pentanoyl, dodecanoyl, stearoyl, and the like; alicyclic alkanoyl of 3–12 carbon atoms, for example, adamantoyl, cyclohexylcarbonyl, cyclopropylcarbonyl or the like; or an unsubstituted or halogen, lower alkoxy or lower alkyl substituted aroyl group derived from an aromatic carboxylic acid such as benzoyl, 3,4,5-trimethoxybenzoyl, 4-chlorobenzoyl, 4-methylbenzoyl, and the like.

The compounds of the invention are characterized by the formula

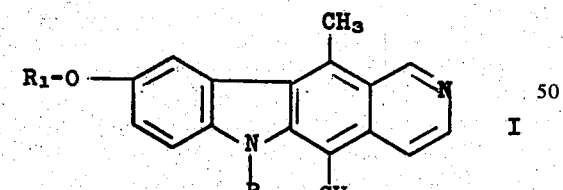

wherein $R_1$ is acyl and $R_2$ is hydrogen or lower alkyl, and pharmaceutically acceptable acid addition salts thereof.

A preferred subgenus of the invention comprises compounds of the formula

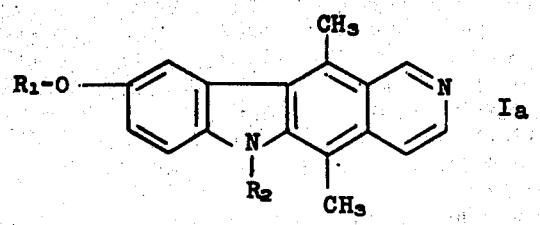

wherein $R_1$ is lower alkanoyl and $R_2$ is as previously described.

A most preferred subgenus comprises compounds of formula Ia wherein $R_1$ is acetyl.

Exemplary of the compounds of formula I are:
9-formyloxy-5,11-dimethyl-6H-pyrido[4,3-b]carbazole;
9-acetyloxy-5,11-dimethyl-6H-pyrido[4,3-b]carbazole;
9-acetyloxy-5,6,11-trimethyl-6H-pyrido[4,3-b]carbazole;
9-propionyloxy-5,11-dimethyl-6H-pyrido[4,3-b]carbazole;
9-propionyloxy5,11-dimethyl-6-ethyl-6H-pyrido[4,3-b]carbazole;
9-(2-methylpropionyloxy)-5,11-dimethyl-6H-pyrido[4,3-b]carbazole;
9-valeroyloxy-5,11-dimethyl-6H-pyrido[4,3-b]carbazole;
9-valeroyloxy-5,11-dimethyl-6-propyl-6H-pyrido[4,3-b]carbazole;
9-caproyloxy-5,11-dimethyl-6H-pyrido[4,3-b]carbazole;
9-caproyloxy-5,6,11-trimethyl-6H-pyrido[4,3-b]carbazole;
9-(4-chlorobenzoyloxy)-5,11-dimethyl-6H-pyrido[4,3-b]carbazole;
9-(3,4,5-trimethoxybenzoyloxy)-5,6,11-trimethyl-6H-pyrido[4,3-b]carbazole;
9-octanoyloxy-5,11-dimethyl-6H-pyrido[4,3-b]carbazole;
9-octanoyloxy-5,11-dimethyl-6-ethyl-6H-pyrido[4,3-b]carbazole;
9-decanoyloxy-5,11-dimethyl-6H-pyrido[4,3-b]carbazole;
9-decanoyloxy-5,6,11-trimethyl-6H-pyrido[4,3-b]carbazole;
9-myristoyloxy-5,11-dimethyl-6H-pyrido[4,3-b]carbazole;
9-lauroyloxy-5,11-dimethyl-6H-pyrido[4,3-b]carbazole;
9-lauroyloxy-5,11-dimethyl-6-propyl-6H-pyrido[4,3-b]carbazole;
9-stearoyloxy-5,11-dimethyl-6H-pyrido[4,3-b]carbazole;
9-benzoyloxy-5,11-dimethyl-6H-pyrido[4,3-b]carbazole;
9-benzoyloxy-5,6,11-trimethyl-6H-pyrido[4,3-b]carbazole;
9-(1-adamantoloxy)-5,11-dimethyl-6H-pyrido[4,3-b]carbazole;
9-(1-adamantoyloxy)-5,6,11-trimethyl-6H-pyrido[4,3-b]carbazole; and the like.

Preferred species are:
9-acetyloxy-5,11-dimethyl-6H-pyrido[4,3-b]carbazole; and
9-acetyloxy-5,6,11-trimethyl-6H-pyrido[4,3-b]carbazole.

The compounds of formula I can also be named as derivatives of ellipticine. Thus, for example, 9-acetyloxy-5,11-dimethyl-6H-pyrido[4,3-b]carbazole can also be referred to as 9-acetyloxyellipticine.

The compounds of the invention can be prepared by a process which comprises reacting 9-hydroxy-5,11-dimethyl-6H-pyrido[4,3-b]carbazole (known as Ellipticine) or a 9-hydroxy-5,11-dimethyl-6-lower alkyl-6H-pyrido[4,3-b]carbazole, with an acylating agent, for example, an acyl halide such as formyl chloride, acetyl chloride, propionyl bromide, valeroyl chloride, octanoyl chloride, decanoyl chloride, myristoyl chloride, lauroyl chloride, stearoyl chloride, benzoyl chloride, 1-adamantoyl chloride, 4-chlorobenzoyl chloride, 3,4,5-trimethoxybenzoyl chloride, and the like, in the presence of a base such as sodium carbonate, potassium carbonate, and the like.

The reaction conditions are not critical. Conveniently, the reaction can be carried out in an inert solvent, i.e., a solvent which is unaffected by and stable to the reactants, products and reaction conditions of the process. Suitable inert solvents will be readily recognized by those skilled in the art and are exemplified by acetone, tetrahydrofuran, and the like. The reaction is carried out at room temperature; however, temperatures below or above room temperature can be utilized. Conveniently, the reaction is carried out at a temperature in the range of about −20° to about 60° and within these limits, at a temperature of from 0° to 40° is preferred.

The reaction product can be recovered by conventional means, for example, by filtration, decantation or the like. Thereafter, the reaction product can be purified by crystallization from a solvent mixture such as tetrahydrofuran/ethyl acetate, methylene chloride/methanol, methanol, and the like.

As already indicated, the starting material 9-hydroxy5,11-dimethyl-6H-pyrido[4,3-b]carbazole is a known compound. The 9-hydroxy-5,11-dimethyl-6-lower alkyl-6H-pyrido[4,3-b]carbazoles are known compounds or can be prepared according to known procedures. For example, 9-methoxy-5,11-dimethyl-6H-pyrido[4,3-b]carbazole is treated with sodium hydride and a lower alkyl halide such as methyliodide, in an aprotic solvent, for example, dimethylformamide, dimethylsulfoxide or the like, at room temperature or higher. The product which forms, i.e., 9-methoxy-5,11-dimethyl-6-lower alkyl-6H-pyrido[4,3-b]carbazole, is then heated in pyridine HCl to yield the corresponding 9-hydroxy-5,11-dimethyl-6-lower alkyl-6H-pyrido[4,3-b]-carbazole.

The useful cytostatic activity of the compounds of formula I can be demonstrated in warm-blooded animals, e.g., mice and rats, utilizing known and accepted procedures. For instance, the useful activity of the compounds of formula I against growing Walker Sarcocarcinoma No. 256 can be demonstrated in rats by a procedure which comprises weighing and dividing rats into groups of 10 animals for each drug and control group. Thereafter, small pieces of minced tumor are implanted by trocar subcutaneously on the ventral surface of the rat. Treatment by administering the test compound subcutaneously, orally or intraperitoneally is started immediately after implantation and continued for 14 consecutive days at 1/5 of the maximum tolerated dose. The rats are weighed and sacrificed on the 15th day after implantation. Each excised tumor is weighed in grams and the tumor weights are averaged for each group of rats. The total body weight gain or loss for the treatment period is also recorded but not reported. The average tumor weight of the untreated controls (C) is divided by the average tumor weight of each treated group (T). The result is expressed as the C/T Index.

The useful activity of the compounds of formula I against growing Sarco-carcinoma-180 can be demonstrated by a procedure which comprises weighing and dividing mice into groups of 8 animals for each drug and control group. Small pieces of Sarco-carcinoma-180 tumors are implanted by trocar subcutaneously on he ventral surface of the mouse. Mice are treated i.p. with 2/5 of the maximum tolerated dose immediately after implantation and then once daily until 8 treatments are given. The mice are weighed and sacrificed 8 days after implantation. The weight of each excised tumor is determined in mg. and averaged for each group of 8 mice. The total body weight gain or loss for the treatment period is recorded. The C/T Index is calculated as described above.

When 9-acetoxy-5,11-dimethyl-6H-pyrido[4,3-b]carbazole is utilized as the test substance in the foregoing procedure at a dose of 20 mg/kg. i.p., the compound demonstrates a C/T Index of 2.83.

The useful activity of the compounds of formula I against growing Ehrlich solid carcinoma can be demonstrated in mice by a procedure which comprises weighing and dividing mice into groups of 8 animals for each drug and control group. A dilution of Ehrlich carcinoma cells is injected subcutaneously on the ventral surgace of the mouse. Mice are treated i.p. with 2/5 of the maximum tolerated dose immediately after implantation and then once daily until 8 treatments are given. The mice are weighed and sacrified 8 days after implantation. The weight of each excised tumor is determined in mg. and averaged for each group of 8 mice. The total body weight gain or loss for the treatment period is recorded. The C/T Index is calculated as described above.

When 9-acetoxy-5,11-dimethyl-6H-pyrido[4,3-b]carbazole is utilized as the test substance in the foregoing procedure at a dose of 20 mg/kg. i.p., the compound demonstrates a C/T Index of 2.28.

The compounds of formula I form pharmaceutically acceptable acid addition salts and such salts are also within the scope of this invention. Thus, the compounds of formula I form acid salts with pharmaceutically acceptable organic acids, such as tartaric acid, citric acid, lactic acid, oxalic acid, succinic acid, maleic acid, acetic acid, and the like, and with inorganic acids such as hydrohalic acids, for example, hydrogen chloride, hydrogen bromide, hydrogen, as well as mineral acids such as sulfuric acid, phosphoric acid, nitric acid, and the like. The addition salts can suitably be prepared by treatment of the carbazole of formula I with an inert solvent with the corresponding acid.

The compounds can be administered internally in the form of conventional pharmaceutical preparations, for example, the bases of formula I or their pharmaceutically acceptable acid addition salts can be administered in conventional enteral or parenteral pharmaceutical preparations containing organic and/or inorganic inert carriers such as water, gelatin, lactose, starch, magnesium stearate, talc, plant oils, gums, alcohol, Vaseline, or the like. The pharmaceutical preparations can be in conventional solid forms, for example, tablets, dragees, suppositories, capsules, or the like, or conventional liquid forms, such as suspensions, emulsions, or the like. If desired, the pharmaceutical preparations can be sterilized and/or contain conventional pharmaceutical adjuvants such as preservatives, stabilizing agents, wetting agents, emulsifying agents, buffers, or salts used to adjust the osmotic pressure. The pharmaceutical preparations can also contain other therapeutically active ingredients.

The following examples further illustrate the invention. All parts are by weight and all temperatures are in degrees Centigrade, unless otherwise mentioned.

EXAMPLE 1

Preparation of 9-hydroxy-5,11-dimethyl-6H-pyrido[4,3-b]carbazole

A mixture of 9-methoxy-5,11-dimethyl-6H-pyrido[4,3-b]carbazole (26 g.) and pyridine hydrochloride (500 g.) was heated to 210° for 40 minutes. The deep red reaction mixture was cooled, diluted with brine (3 liters) and the resulting precipitate (9-hydroxy-5,11-dimethyl-6H-pyrido[4,3-b]carbazole hydrochloride) was collected by filtration. The salt was dissolved in hot water and the solution was filtered to remove any tarry material that might be present. The cooled solution was added slowly to a stirred saturated sodium bicarbonate solution (1.5 liters). The precipitate was filtered and washed well with cold water. The dried solids (24 g.) were placed in a Sohxlet and extracted using 4 liters of tetrahydrofuran. The extract was concentrated to 1.2 liters and the product was allowed to crystallize to give 20.8 g. (85%) of 9-hydroxy-5,11-dimethyl-6H-pyrido[4,3-b]carbazole, m.p. 307°–309° (vac.).

EXAMPLE 2

Preparation of 9-acetoxy-5,11-dimethyl-6H-pyrido[4,3-b]carbazole

A solution of 9-hydroxy-5,11-dimethyl-6H-pyrido[4,3-b]carbazole (10 g.) in acetic anhydride (75 ml.) and acetyl chloride (25 ml.) was stirred at room temperature for 2 hours. The reaction mixture was poured into excess NaHCO$_3$ solution and stirred for 10 minutes. The resulting precipitate was removed by filtration and was washed well with water. The dried solids (10 g.; 86%) were dissolved in tetrahydrofuran and the solution was charcoaled. Crystallization from tetrahydrofuran-ethyl acetate mixture afforded 9-acetoxy-5,11-dimethyl-6H-pyrido[4,3-b]carbazole (8.3 g.; 75%), m.p. 303°–304°.

EXAMPLE 3

Preparation of 9-dodecanoyloxy-5,11-dimethyl-6H-pyrido[4,3-b]carbazole 1.65 g. of lauroyl chloride was added to a stirred suspension of 1.3 g. of 9-hydroxy-5,11-dimethyl-6H-pyrido[4,3-b]carbazole and 5.0 g. of Na$_2$CO$_3$ in 75 ml. of acetone. After 2 hours (the initial reddish purple color had changed to a pale yellow in 1 1/2 hours) water was slowly added to a final total volume of 600 ml. The precipitate was collected by filtration and was washed with hot water. The dried solid was crystallized from methylene chloride-methanol to give 1.63 g. of yellow crystalline 9-dodecanoyloxy-5,11-dimethyl-6H-pyrido[4,3-b]carbazole, m.p. 188°–190° (74%). The analytically pure material melted at 189°–190.5°.

EXAMPLE 4

In a manner analogous to Example 3, the following compounds set out in Table I were prepared:

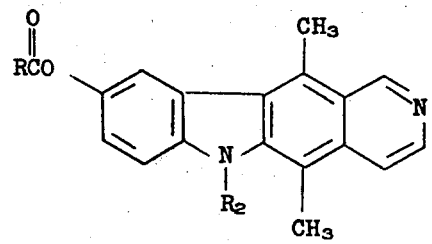

9-ACYLOXY-5,11-DIMETHYL-6H-PYRIDO [4,3-b] CARBAZOLES

| Ex. | Compound | R | R$_2$ | Yield | MP | Crystallization Solvents |
|---|---|---|---|---|---|---|
| 4 | 9-Acetoxy-5,11-dimethyl-6H-pyrido-[4,3-b]carbazole | CH$_3$ | H | 86% | 303–304° (vac) | THF-EtOAc |
| 5 | 9-Propionyloxy-5,11-dimethyl-6H-pyrido[4,3-b]carbazole | CH$_3$CH$_2$— | H | 80% | 280–281° (vac) | THF-EtOAc |
| 6 | 9-(2-Methylpropionyloxy)-5,11-dimethyl-6H-pyrido[4,3-b]carbazole | (CH$_3$)$_2$CH— | H | 89% | 304–305° (vac) | THF-EtOAc |
| 7 | 9-Hexanoyloxy-5,11-dimethyl-6H-pyrido-[4,3-b]carbazole | CH$_3$(CH$_2$)$_4$ | H | 80% | 235–236° (vac) | THF-EtOAc |
| 8 | 9-Dodecanoyloxy-5,11-dimethyl-6H-pyrido-[4,3-b]carbazole | CH$_3$(CH$_2$)$_{10}$ | H | 74% | 189–190.5° | CH$_2$Cl$_2$—MeOH |
| 9 | 9-Stearoyloxy-5,11-dimethyl-pyrido-[4,3-b]carbazole | CH$_3$(CH$_2$)$_{16}$ | H | 63% | 183–185° | CH$_2$Cl$_2$—MeOH |
| 10 | 9-(1-Adamantoyloxy)-5,11-dimethyl-6H-pyrido [4,3-b]carbazole | adamantyl | H | 34% | 350° (vac) | MeOH |
| 11 | 9-Acetoxy-5,6,11-trimethyl-6H-pyrido-[4,3-b]carbazole | CH$_3$— | CH$_3$— | 70% | 198–199° | CH$_2$Cl$_2$—EtOAc |
| 12 | 9-Benzoyl-5,11-dimethyl-6H-pyrido-[4,3-b]carbazole | phenyl | H | 88% | 294–296° | MeOH |
| 13 | 9-Hexanoyloxy-5,6,11-trimethyl-6H-pyrido-[4,3-b]carbazole | CH$_3$(CH$_2$)$_4$ | CH$_3$— | 67% | 151–152° | EtOAc |

EXAMPLE 5

Preparation of
9-methoxy-5,6,11-trimethyl-6H-pyrido[4,3-b]carbazole

A solution of 10.0 g. of 9-methoxy-5,11-dimethyl-6H-pyrido[4,3-b]carbazole in dry dimethylformamide (120 ml.) was treated with 2.18 g. of sodium hydride (50% oil dispersion) and stirred for 5 minutes. 5.1 g. of methyl iodide in dimethylformamide (70 ml.) was added rapidly and the mixture was stirred overnight at room temperature. The solution was poured into 1 l. of $H_2O$ and extracted with $CHCl_3$ (6 × 400 ml.). The $CHCl_3$ extract was dried over sodium sulfate and was passed through a short column of Woelm basic alumina (120 g., grade III) and then was evaporated in vacuo. Crystallization of the residue from ethyl acetate afforded 6.8 g. of 9-methoxy-5,6,11-trimethyl-6H-pyrido[4,3-b]carbazole, m.p. 153–154.

Utilizing the procedure described in Example 5, the following compounds can be prepared:

from 9-methoxy-5,11-dimethyl-6H-pyrido[4,3-b]carbazole and ethyl iodide, there can be prepared 9-methoxy-5,11-dimethyl-6-ethyl-6H-pyrido[4,3-b]carbazole;

from 9-methoxy-5,11-dimethyl-6H-pyrido[4,3-b]carbazole and propyl iodide, there can be prepared 9-methoxy-5,11-dimethyl-6-propyl-6H-pyrido[4,3-b]carbazole;

from 9-methoxy-5,11-dimethyl-6H-pyrido[4,3-b]carbazole and butyl iodide, there can be prepared 9-methoxy-5,11-dimethyl-6-butyl-6H-pyrido[4,3-b]carbazole

EXAMPLE 6

Preparation of
9-hydroxy-5,6,11-trimethyl-6H-pyrido[4,3-b]carbazole

A mixture of 6.5 g. of 9-methoxy-5,6,11-trimethyl-6H-pyrido[4,3-b]carbazole in 120 g. of pyridine HCl was heated at 210° for 1.5 hours. The reaction mixture was cooled and worked up as in Example 1. The product that precipitated was filtered and dried to give 6.0 g. of product. The dried solids were extracted (Sohxlet) into methyl alcohol (1 l.) and the extract on cooling yielded 5.2 g. of 9-hydroxy-5,6,11-trimethyl-6H-pyrido[4,3-b]carbazole, m.p. 336°–337° (vac). Crystallization from dimethylformamide gave 9-hydroxy-5,6,11-trimethyl-6H-pyrido[4,3-b]carbazole, m.p. 337°–338°.

Utilizing the procedure described in Example 6, the following compounds can be prepared:

from 9-methoxy-5,11-dimethyl-6-ethyl-6H-pyrido[4,3-b]carbazole, there can be prepared 9-hydroxy-5,11-dimethyl-6-ethyl-6H-pyrido[4,3-b[carbazole;

from 9-methoxy-5,11-dimethyl-6-propyl-6H-pyrido[4,3-b]carbazole, there can be prepared 9-hydroxy-5,11-dimethyl-6-propyl-6H-pyrido[4,3-b]carbazole;

from 9-methoxy-5,11-dimethyl-6-butyl6H-pyrido[4,3-b]carbazole, there can be prepared 9-hydroxy-5,11-dimethyl-6-butyl-6H-pyrido[4,3-b]carbazole.

EXAMPLE 7

| Capsule Formulation | Per Capsule |
|---|---|
| 9-Acetoxy-5,11-dimethyl-6H-pyrido[4,3-b]-carbazole (also referred to as 9-acetoxyellipticine) | 250 mg. |
| Lactose | 60 mg. |
| Corn Starch | 35 mg. |
| Magnesium Stearate | 5 mg. |
| Total Weight | 350 mg. |

All of the ingredients are mixed until thoroughly blended in a suitable size container. Then, the powder is filled into No. 2, two piece, hard shell gelatin capsules to an approximate fill weight of 350 mg. using a Parke Davis capsulating machine. (Any similar type machine may be used.)

EXAMPLE 8

| Tablet Formulation | Per Tablet |
|---|---|
| 9-Acetoxy-5,11-dimethyl-6H-pyrido[4,3-b]-carbazole | 200 mg. |
| Dicalcium Phosphate Dihydrate, Unmilled | 235 mg. |
| Corn Starch | 70 mg. |
| FD&C Yellow No. 5 - Aluminum Lake 25% | 2 mg. |
| A mixture of di and tri fatty acid esters of glycerin | 25 mg. |
| Calcium Stearate | 3 mg. |
| Total Weight | 535 mg. |

All the ingredients are mixed thoroughly and passed through a Model "D" Fitzmill with a No. 1A screen, medium speed. Then, the mixture is remixed and slugged. The slugs are screened on an Oscillator through a No. 14 mesh screen and compressed on an "E" machine into tablets of an approximate weight of 535 mg.

EXAMPLE 9

| Capsule Formulation | Per Capsule |
|---|---|
| 9-Acetoxy-5,11-dimethyl-6H-pyrido[4,3-b]-carbazole | 50 mg. |
| Lactose, USP | 125 mg. |
| Corn Starch, USP | 30 mg. |
| Talc, USP | 5 mg. |

9-Acetoxy-5,11-dimethyl-6H-pyrido[4,3-b]carbazole is mixed with lactose and corn starch in a suitable mixer. The mixture is further blended by passing through a Fitzpatrick Comminuting Machine with a No. 1A screen with knives forward. The blended powder is returned to the mixer, the talc is added and blended thoroughly. The mixture is filled into No. 4 hard shell gelatin capsules on a Parke Davis capsultating machine.

EXAMPLE 10

| Tablet Formulation | Per Tablet |
|---|---|
| 9-Acetoxy-5,11-dimethyl-6H-pyrido[4,3-b]-carbazole | 25 mg. |
| Dicalcium Phosphate Dihydrate, Unmilled | 175 mg. |
| Corn Starch | 24 mg. |
| Magnesium Stearate | 1 mg. |
| Total Weight | 225 mg. |

9-Acetoxy-5,11-dimethyl-6H-pyrido[4,3-b]carbazole and corn starch are mixed together and passed through a No. 00 screen in Model "J" Fitzmill with hammers forward. This premix is then mixed with dicalcium phosphate and one-half of the magnesium stearate, passed through a No. 1A screen in Model "J" Fitzmill with knives forward, and slugged. The slugs are passed through a No. 2A plate in a Model "D" Fitzmill at slow speed with knives forward, and the remaining magnesium stearate is added. The mixture is mixed and compressed into tablets of an approximate weight of 225 mg.

EXAMPLE 11

| Tablet Formulation | Per Tablet |
|---|---|
| 9-Acetoxy-5,11-dimethyl-6H-pyrido[4,3-b]carbazole | 100 mg. |
| Lactose, USP | 202 mg. |
| Corn Starch, USP | 80 mg. |
| Prehydrolyzed Corn Starch | 20 mg. |
| Calcium Stearate | 8 mg. |
| Total Weight | 410 mg. |

9-Acetoxy-5,11-dimethyl-6H-pyrido[4,3-b]carbazole, lactose, corn starch and prehydrolyzed corn starch are blended in a suitable mixer. The mixture is granulated to a heavy paste with water and the moist mass is passed through a No. 12 screen. Then, it is dried overnight at 110°F. The dried granules are passed through a No. 16 screen and transferred to a suitable mixer. The calcium stearate is added and mixed until uniform. The mixture is compressed at a tablet weight of 410 mg. using tablet punches having a diameter of approximately ⅜ inch. (Tavlets may be either flat or biconvex and may be scored if desired.)

EXAMPLE 12

| Tablet Formulation | Per Tablet |
|---|---|
| 9-Acetoxy-5,11-dimethyl-6H-pyrido-[4,3-b]carbazole | 500 mg. |
| Corn Starch | 30 mg. |
| Lactose | 88 mg. |
| Gelatin | 12 mg. |
| Talcum | 15 mg. |
| Magnesium Stearate | 5 mg. |
| Total Weight | 650 mg. |

9-Acetoxy-5,11-dimethyl-6H-pyrido[4,3-b]carbazole and lactose are thoroughly mixed in suitable blending equipment and granulated with a 10% gelatin solution. The moist mass is passed through a No. 12 screen, and the granules are dried on paper-lined trays overnight. The dried granules are passed through a No. 14 screen and placed in a suitable mixer. The talcum and magnesium stearate are added and blended. The granulation is compressed into tablets weighing approximately 650 mg. each, using punches having an approximate diameter of 12.7 mm. (½ inch). The final tablet thickness is about 5.1 mm.

EXAMPLE 13

| Parenteral Formulation | Per cc. |
|---|---|
| 9-Acetoxy-5,11-dimethyl-6H-pyrido-[4,3-b]carbazole | 5.0 mg. |
| Benzyl Alcohol | 0.1 cc. |
| Lactic Acid, USP | 1.5 mg. |
| Water for Injection, USP q.s. ad | 1 cc. |

In a clean glass or glass-lined vessel, 800 cc. of Water for Injection are heated to 90°C. Then, the water is cooled to 50°–60°C., and benzyl alcohol is added and dissolved with stirring. The solution is allowed to cool to room temperature. 5.0 G. of acetoxy-5,11-dimethyl-6H-pyrido[4,3-b]carbazole and 1.5 grams of lactic acid are added under an atmosphere of nitrogen and stirred until completely dissolved. Sufficient Water for Injection is added to make a total volume of 1,000 cc. This solution is then filtered through an 02 Selas candle, filled into suitable size ampuls, gassed with nitrogen and sealed.

We claim:

1. A compound of the formula

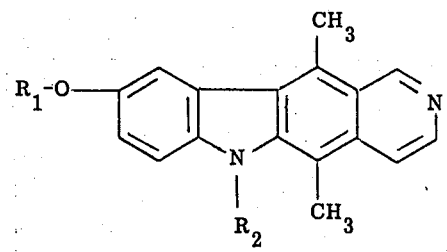

wherein $R_1$ is alkanoyl of 1 to 18 carbon atoms, alicyclic alkanoyl of 3 to 12 carbon atoms, benzoyl, 3,4,5-trimethoxybenzoyl, 4-chlorobenzoyl, or 4-methylbenzoyl and $R_2$ is hydrogen or lower alkyl of 1 to 7 carbon atoms, or a pharmaceutically acceptable acid addition salt thereof.

2. A compound in accordance with claim 1, wherein $R_1$ is lower alkanoyl of 1 to 18 carbon atoms.

3. A compound in accordance with claim 2, wherein $R_1$ is acetyl.

4. A compound in accordance with claim 1, 9-acetoxy-5,11-dimethyl-6H-pyrido[4,3-b]carbazole.

5. A compound in accordance with claim 1, 9-propionyloxy-5,11-dimethyl-6-pyrido[4,3-b]carbazole.

6. A compound in accordance with claim 1, 9-(2-methylpropionyloxy)-5,11-dimethyl-6H-pyrido[4,3-b]carbazole.

7. A compound in accordance with claim 1, 9-hexanoyloxy-5,11-dimethyl-6H-pyrido[4,3-b]carbazole.

8. A compound in accordance with claim 1, 9-dodecanoyloxy-5,11-dimethyl-6H-pyrido[4,3-b]carbazole.

9. A compound in accordance with claim 1, 9-stearoyloxy-5,11-dimethyl-6H-pyrido[4,3-b]carbazole.

10. A compound in accordance with claim 1, 9-(1-adamantoyloxy)-5,11-dimethyl-6H-pyrido[4,3-b]carbazole.

11. A compound in accordance with claim 1, 9-acetoxy-5,6,11-trimethyl-6H-pyrido[4,3-b]carbazole.

12. A compound in accordance with claim 1, 9-benzoyl-5,11-dimethyl-6H-pyrido[4,3-b]carbazole.

13. A compound in accordance with claim 1, 9-hexanoyloxy-5,6,11-trimethyl-6H-pyrido[4,3-b]carbazole.

* * * * *